(12) United States Patent
Xu

(10) Patent No.: US 8,185,187 B2
(45) Date of Patent: May 22, 2012

(54) MAGNETIC RESONANCE LMETHOD AND APPARATUS WITH GATED SHIMMING OF THE BASIC MAGNETIC FIELD

(75) Inventor: Jian Xu, Kew Gardens, NY (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 295 days.

(21) Appl. No.: 12/402,055

(22) Filed: Mar. 11, 2009

(65) Prior Publication Data

US 2010/0234723 A1    Sep. 16, 2010

(51) Int. Cl.
*A61B 5/05* (2006.01)

(52) U.S. Cl. ...................................................... 600/413

(58) Field of Classification Search ........................ None
See application file for complete search history.

(56) References Cited

U.S. PATENT DOCUMENTS

| | | | |
|---|---|---|---|
| 5,830,143 A * | 11/1998 | Mistretta et al. | 600/420 |
| 5,910,112 A * | 6/1999 | Judd et al. | 600/410 |
| 6,937,696 B1 * | 8/2005 | Mostafavi | 378/95 |
| 2002/0032377 A1 * | 3/2002 | Thesen | 600/419 |
| 2003/0100827 A1 * | 5/2003 | Deimling | 600/410 |
| 2004/0092809 A1 * | 5/2004 | DeCharms | 600/410 |

OTHER PUBLICATIONS

Prospective acquisition correction for head motion with image-based tracking for real time fMRI, Magnetic Resonance in Medicine 44:457-465 (2000), henceforth referred to as Thesen.*

* cited by examiner

*Primary Examiner* — Brian Casler
*Assistant Examiner* — Saurel J Selkin
(74) *Attorney, Agent, or Firm* — Schiff Hardin LLP

(57) ABSTRACT

In the acquisition of magnetic resonance imaging or spectroscopic data, 2D PACE is employed to identify an acceptance or shimming window within which the magnetic resonance data are acquired, and to trigger the acquisition of the magnetic resonance data at the same position of the patient's diaphragm in each respiratory cycle. The patient is thereby allowed to freely breath during the data acquisition procedure, but the acquisition of the magnetic resonance data is always able to take place with the patient's diaphragm in the same physical position in each respiratory cycle.

6 Claims, 3 Drawing Sheets

MAGNETIC RESONANCE LMETHOD AND APPARATUS WITH GATED SHIMMING OF THE BASIC MAGNETIC FIELD

BACKGROUND OF THE INVENTION

1. Field of the Invention

The present invention relates to methods and apparatuses for implementing magnetic resonance procedures, including imaging and spectroscopy procedures, wherein the basic magnetic field is shimmed.

2. Description of the Prior Art

Magnetic resonance imaging and spectroscopy are patient examining modalities wherein magnetic resonance signals are caused to be generated in and emitted from an examination subject, and the emitted magnetic resonance signals are detected. Many known techniques are available for generating and detecting such signals. Imaging or spectroscopic information is then derived from these signals, also in a known manner.

In all magnetic resonance examinations, the patient is placed in a strong magnetic field that causes the nuclear spins in the examination subject to be aligned. Radio-frequency energy is then radiated into the patient which causes the nuclear spins to be displaced from the aligned orientation, so that the spins precess with a frequency that is dependent on the substance containing the precessing nuclei.

The strong magnetic field that initially aligns the nuclei (nuclear spins) is known as the B0 field, and is also called the basic magnetic field. This magnetic field is generally a static magnetic field, and must exhibit a high degree of homogeneity in the examination volume from which the magnetic resonance signals are acquired. Since the environment in which a particular magnetic resonance apparatus is installed, and the presence of the patient in the magnetic resonance apparatus, effect the homogeneity of the basic magnetic field, it is not possible to precisely and reproducibly set or fix the homogeneity of the basic magnetic field prior to installation of the magnetic resonance apparatus, and for many types of magnetic resonance examinations, the basic magnetic field must be adjusted immediately prior to the examination itself. The adjustment of the basic magnetic field is known as "shimming."

A substantial number of clinical and research magnetic resonance scans are unusable due to patient motion that occurs during the scanning. In particular, magnetic resonance spectroscopy studies in the abdomen are very difficult to implement in practice, and require very good shimming of the basic magnetic field. Various techniques have been proposed to address this problem, including ECG triggering in order to gate the shimming at the same cardiac phase in each image acquisition (scan), as well as the breath-holding technique. The latter technique, however, cannot be used for patients who are unable to hold their breath, since conventional shim sequences usually employ 3D data acquisitions, which require a relatively long scan time. Very special need for techniques that allow the patient to freely breath during the shimming measurements that are made with the examination subject in the magnetic resonance apparatus.

Artifacts due to body motion such as respiratory motion are a problem in the field of magnetic resonance imaging, separate from the aforementioned shimming problem. Techniques are known to acquire magnetic resonance data, while allowing free breathing on the part of the patient, and the image data are then corrected according to motion compensation algorithms or other techniques. One such motion compensation technique is the 2D perspective acquisition correction (PACE) technique that is commercially available from Siemens Healthcare in a software package for operating the Magnetom Avanto. The PACE technique represents a consolidated and extremely rapid technique using embedded navigators to estimate and correct the motion of the diaphragm in real-time, without the need for additional hardware. This technique has proven successful as long as the organ displacement is modest. In this technique, the gradients are adjusted rapidly for rotations during scanning, and the RF slab select and phase errors due to the translations are also corrected in real-time. The resulting k-space data are therefore already corrected for motion, and the image can be reconstructed in a conventional manner, without the need for additional post-processing, to yield a motion-corrected image immediately at the display console. Frequency drift and first-order shim errors are also corrected in real-time.

SUMMARY OF THE INVENTION

An object of the present invention is to provide a shimming technique that does not require breath holding on the part of the patient. The above object is achieved in accordance with the present invention by implementing double triggering using 2D PACE and ECG gating in 3D single-echo and multi-echo FLASH or DESS sequences, to shim the basic magnetic field.

The above object also is achieved by using the 2D PACE software in magnetic resonance imaging or magnetic resonance spectroscopy studies to ensure that the respective image acquisitions (scans) are made with the same shimming offsets and the same RF center frequency.

More specifically, the 2D PACE technique is used to identify a shimming window or an "acceptance window" that is automatically determined by real-time evaluation of the navigator signal that is employed in 2D PACE. This window is determined to be at a time within the respiratory cycle wherein displacement of the organ under examination is minimal. The shimming is undertaken in this window, followed by data acquisition in the window.

DESCRIPTION OF THE PREFERRED EMBODIMENTS

Figure 1:
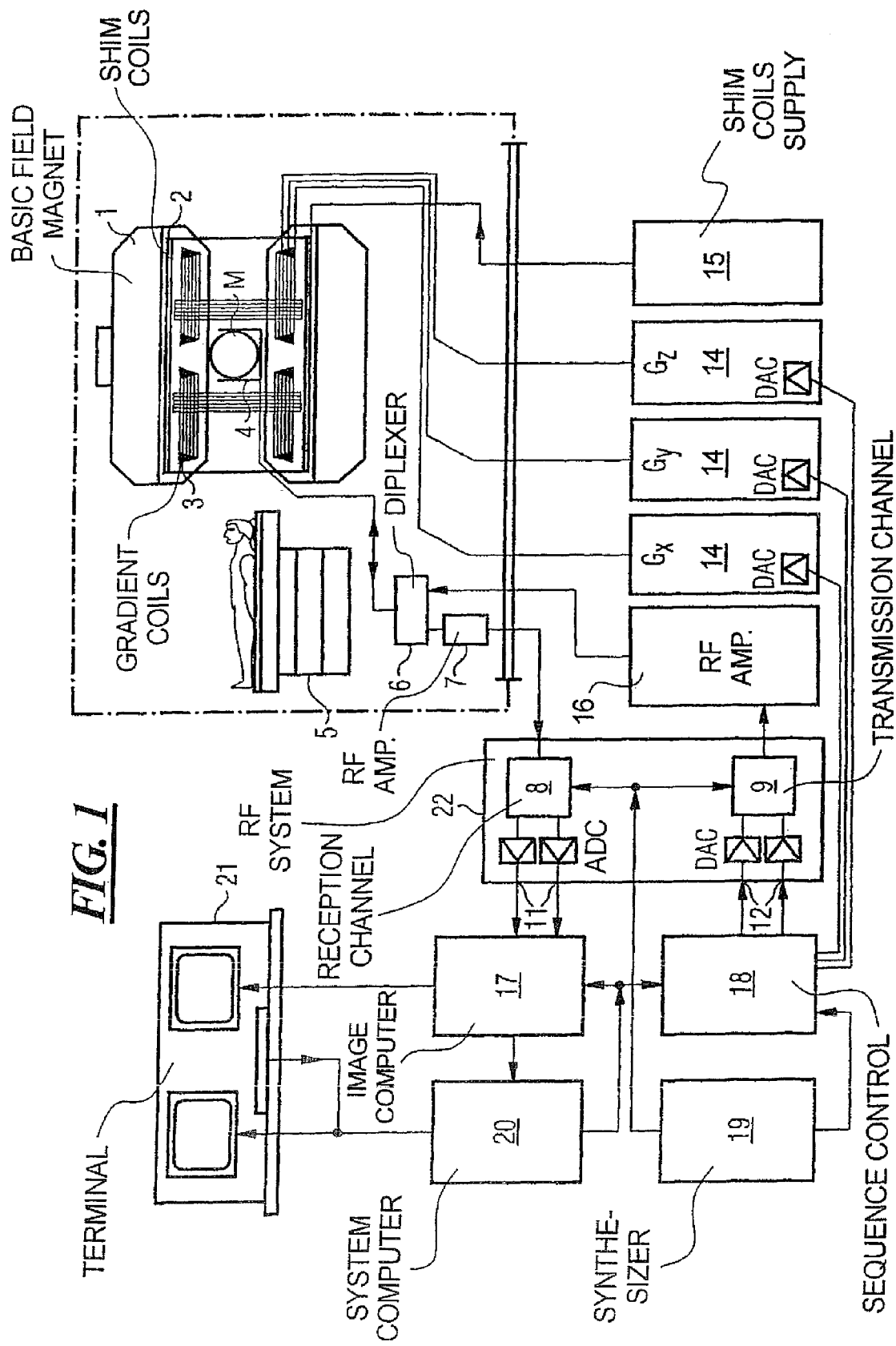
FIG. 1 is a block diagram showing the basic components of a magnetic resonance apparatus constructed and operated in accordance with the principles of the present invention.

FIG. 1 shows a schematic representation of a magnetic resonance apparatus for generation of a magnetic resonance image of a subject according to the present invention. The design of the nuclear magnetic resonance tomography apparatus corresponds to the design of a conventional tomography apparatus, with the exceptions noted below. A basic magnetic field 1 generates a temporally constant, strong magnetic field for polarization or, respectively, alignment of the nuclear spins in the examination region of a subject (such as, for example, a portion of a human body to be examined) on a patient table 5. The high homogeneity of the basic magnetic field that is required for the nuclear magnetic resonance measurement is defined in a spherical measurement volume M into which the portions of the human body to be examined are introduced. Components known as shim plates (not shown) made from ferromagnetic material are applied at suitable points to support the homogeneity requirements and in particular to eliminate temporally invariable influences. Temporally variable influences are eliminated by shim coils 2 that are controlled by a shim power supply 15.

A cylindrical gradient coil system 3 formed by three sub-windings is embodied in the basic field magnet 1. Each sub-winding is provided by an amplifier 14 with current to generate a linear gradient field in the respective direction of the Cartesian coordinate system. The first sub-winding of the gradient field system 3 thereby generates a gradient $G_x$ in the x direction; the second sub-winding generates a gradient $G_y$ in the y direction; and the third sub-winding generates a gradient $G_z$ in the z direction. Each amplifier 14 has a digital/analog converter that is activated by a sequence controller 18 for accurately timed generation of the gradient pulses.

Located within the gradient coils 3 is a radio-frequency antenna 4 that converts the radio-frequency pulses emitted by a radio-frequency power amplifier 16 into an alternating magnetic field to excite the nuclei and align the nuclear spins of the subject to be examined or, respectively, of the region of the subject to be examined. The alternating field emanating from the precessing nuclear spins, i.e. normally the nuclear spin echo signals caused by a pulse sequence made up from one or more radio-frequency pulses and one or more gradient pulses, is converted into a voltage that is supplied via an amplifier 7 to a radio-frequency reception channel 8 of a radio-frequency system 22. The radio-frequency system 22 furthermore has a transmission channel 9 in which the radio-frequency pulses for the excitation of the nuclear magnetic resonance signals are generated. In the sequence controller 18, the respective radio-frequency pulses are represented digitally as a series of complex numbers based on a pulse sequence predetermined by the system controller 20. This number series is supplied as a real part and as an imaginary part via respective inputs 12 to a digital/analog converter in the radio-frequency system 22, and from this to a transmission channel 9. In the transmission channel 9 the pulse sequences are modulated to a radio-frequency carrier signal whose base frequency corresponds to the resonance frequency of the nuclear spins in the measurement volume.

The switching from transmission operation to reception operation ensues via a transmission-reception diplexer 6. The radio-frequency antenna 4 radiates the radio-frequency pulses for excitation of the nuclear spins into the measurement volume M and samples resulting echo signals. The correspondingly acquired nuclear magnetic resonance signals are phase-sensitively demodulated in a reception channel 8 of the radio-frequency system 22 and are converted into real part and imaginary part by a respective analog/digital converter. Data representing the real part and the imaginary part are supplied via respective outputs 11 to an image computer 17. An image is reconstructed by the image computer 17 from the measurement data acquired in this manner. The administration of the measurement data, the image data and the control programs ensues through the system computer 20. The sequence controller 18 monitors the generation of the respective desired pulse sequences and the corresponding scanning of k-space based on a specification with control programs. The sequence controller 18 in particular controls the accurately timed switching of the gradients, the emission of the radio-frequency pulses with defined phase and amplitude and the acquisition of the nuclear magnetic resonance signals.

The time base for the radio-frequency system 22 and the sequence controller 18 is provided by a synthesizer 19. The selection of corresponding control programs to generate a magnetic resonance image, as well as the representation of the generated magnetic resonance image; ensue via a terminal 21 that has a keyboard and one or more monitors.

Figure 2:
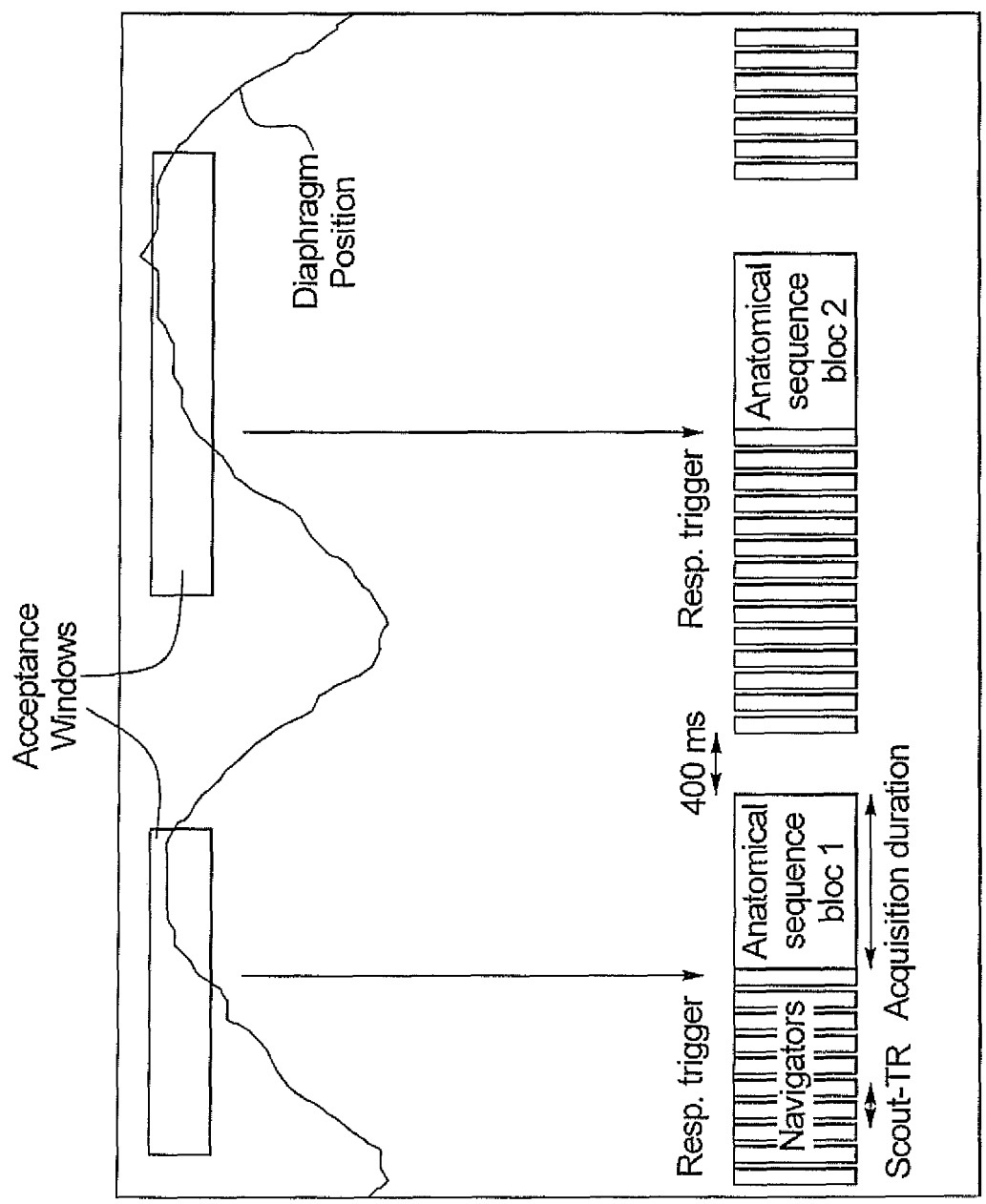
FIG. 2 schematically illustrates detection of a shimming window in accordance with the present invention, using 2D PACE.

Either the system computer 20 or the sequence control 18 in the apparatus of FIG. 1 is programmed (configured) in accordance with the present invention to implement a gated shimming procedure, as schematically illustrated in FIG. 2.

Prior to a shimming acquisition, the above-described 2D PACE sequence acquires fast radio echo images while the patient is breathing freely, with data acquisition being triggered at the quiet and expiration phase of the respiratory cycle according to a shimming window. The shimming window is determined by the vertical width of the displacement of the diaphragm. After a short learning phase, the patient's breathing pattern is analyzed electronically, such as by using a neural network, and the central position of the shimming window (two of which are shown in FIG. 2) is automatically calculated. The real-time evaluation of the navigator signal allows for an immediate start of the acquisition of imaging or spectroscopic data as soon as the diaphragm has reached a position within the shimming window. The navigator image needed for this determination is acquired in 100 ms using a low-resolution gradient echo sequence with a low flip angle. This leaves the magnetization in the volume of interest practically undisturbed. This ensures that the magnetization is almost unsaturated.

To minimize tissue displacement, a segment approach could be measured within a breathing cycle. Motion is monitored and tracked for every TR (repetition time), or over several TR of a sequence such as 3D FLASH or 3D DESS. Estimates of the zero and first order B0 (basic magnetic field) offsets (due to frequency drift and first order shim values) are made, and a correction is fed back to adjust the gradients, the RF center frequency, and the shim offsets. Adjusting for the B0 offsets improves the navigator estimates and the image quality.

To reduce the scan time, a segmentation technology can be used.

The triggering conditions are illustrated in FIG. 2. A change in signal intensity of the rectangular region is used to determine the position of the diaphragm. The real-time evaluation of the navigator signal allows the immediate start of the data acquisition portion, as soon as the diaphragm has reached the position within the acceptance window. With the PACE implementation, MRI or MRS sequences can be triggered with respect to the quiet and expiration phase, with either an automatically or manually defined shimming window. Such triggering will be in exactly the same position as in the previous shimming environment.

In 2D PACE, an image is acquired using a low-resolution gradient echo sequence with a low flip angle, as noted above, so that the magnetization of the volume of interest is substantially undisturbed, and the magnetization is almost unsaturated. Nevertheless, it is recommended to always try to place the PACE rectangle beneath the volume of interest for the examinations.

The basic features of the 2D PACE technique are that the aforementioned learning phase requires approximately five respiratory cycles. The actual scan time is approximately (5+X), wherein X is an average respiratory period. As soon as the system detects a rising signal (on said expiration), the acceptance window is displayed as a colored box. If the detected diaphragm displacement, as indicated by the curve designated diaphragm position, falls within the acceptance window, the basic anatomical measurement block (sequence) is executed, namely the "imaging phase" or the "MRS measurement phase." Since a 2D image provides more information than a single line, the technique disclosed herein is very robust, making free breathing abdominal MR imaging and MR spectroscopy a clinical reality.

The time needed to acquire an image for 2D PACE is approximately 100 ms. 2D PACE is best suited for abdominal MRS, since the increase in scan time is insignificant.

Figure 3:
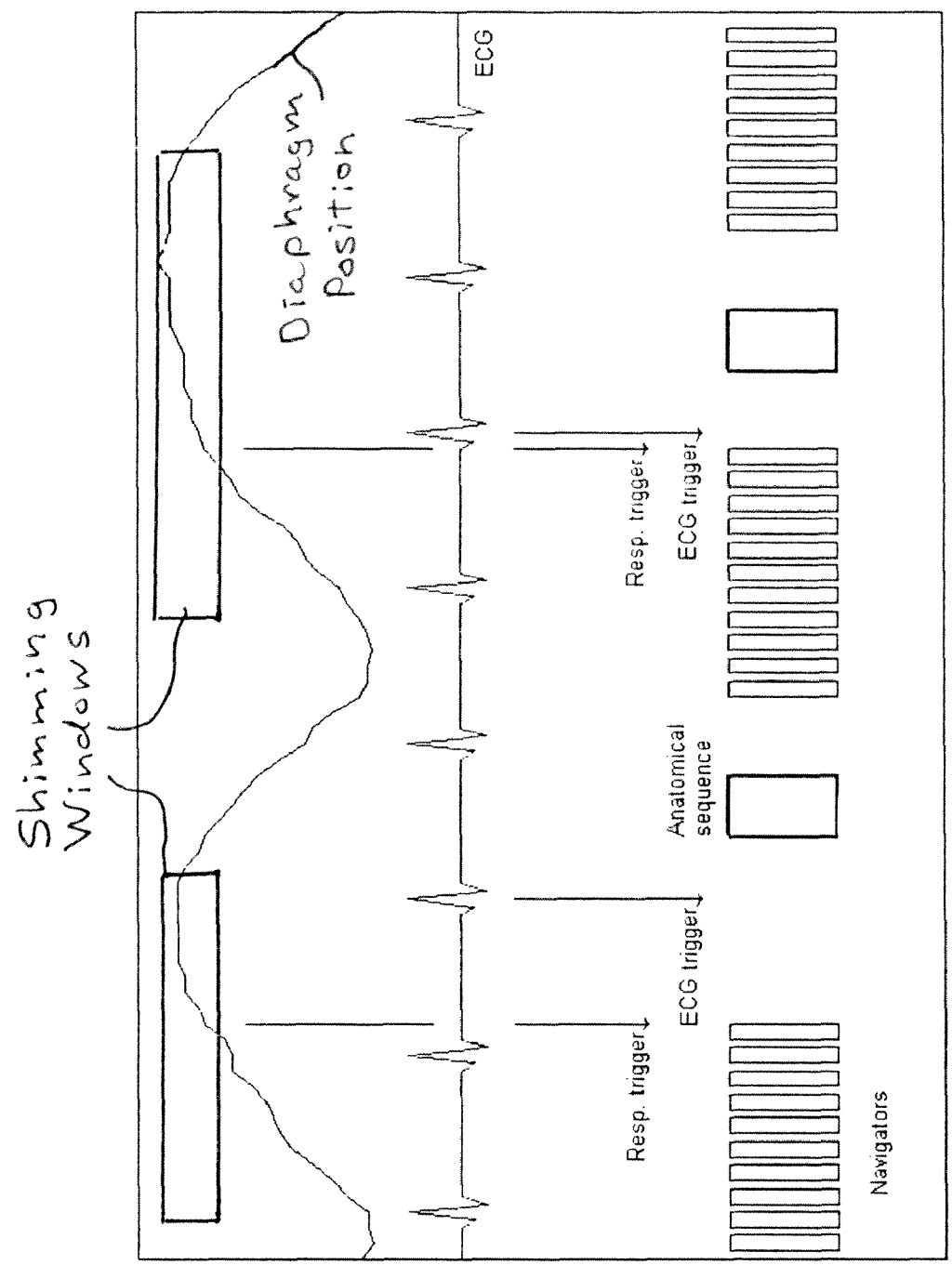
FIG. 3 schematically illustrates a further embodiment of the present invention wherein a shimming window is detected using 2D PACE and data acquisition is triggered using an ECG signal.

As shown in FIG. 3, double triggering (2D PACE plus ECG gating) is used in 3D single and multi-echo FLASH or DESS sequences, to shim the B0 field. For this embodiment, and ECG signal is acquired from the patient using an ECG monitor, as shown in FIG. 1. 2D PACE also can be used in MR imaging or MR spectroscopy studies to ensure that the acquisitions are made with the same shimming offsets and the same RF center frequency.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for acquiring magnetic resonance data, comprising the steps of:
   operating a magnetic resonance data acquisition apparatus with a magnetic resonance data acquisition sequence selected from the group consisting of a double echo steady state (DESS) sequence and a fast low angle shot (FLASH) sequence, to acquire magnetic resonance data in a magnetic resonance data acquisition sequence from a freely breathing patient located in a basic magnetic field generated in the magnetic resonance apparatus;
   monitoring respiration of the examination subject in the magnetic resonance data acquisition apparatus using a two-dimensional prospective acquisition correction (2D PACE) signal to identify a shimming window that is identically correlated with the same physical, mechanical position of the patient's diaphragm in the respiratory cycle;
   acquiring an electrocardiogram (ECG) from the patient in the magnetic resonance data acquisition apparatus;
   triggering acquisition of said magnetic resonance data with said magnetic resonance data acquisition sequence using said 2D PACE signal and said ECG to cause said magnetic resonance data to be acquired in said magnetic resonance data acquisition sequence at said same position of the patient's diaphragm in multiple respiratory cycles and only within said shimming window; and
   in said shimming window, adjusting a homogeneity of said basic magnetic field using said DESS sequence or said FLASH sequence.

2. A method as claimed in claim 1 further comprising employing navigator signals in 2D PACE to trigger said data acquisition.

3. A method as claimed in claim 1 further comprising acquiring magnetic resonance image data as said magnetic resonance data with said magnetic data acquisition sequence.

4. A method as claimed in claim 1 further comprising acquiring magnetic resonance spectroscopic data as said magnetic resonance data with said magnetic data acquisition sequence.

5. A magnetic resonance system comprising:
   a magnetic resonance data acquisition apparatus;
   a controller configured to operate said magnetic resonance data acquisition apparatus with a magnetic resonance data acquisition sequence selected from the group consisting of a double echo steady state (DESS) sequence and a fast low angle shot (FLASH) sequence, to acquire magnetic resonance data in said magnetic resonance data acquisition sequence from a freely breathing patient located in a basic magnetic field generated in the magnetic resonance apparatus;
   said controller being configured to monitor respiration of the examination subject in the magnetic resonance data acquisition apparatus using a two-dimensional prospective acquisition correction (2D PACE) signal to identify a shimming window that is identically correlated with the same physical, mechanical position of the patient's diaphragm in the respiratory cycle;
   an electrocardiogram (ECG) monitor that acquires an ECG from the patient in the magnetic resonance data acquisition apparatus;
   said controller being configured to trigger acquisition of said magnetic resonance data with said magnetic resonance data acquisition sequence using said 2D PACE signal and said ECG to cause said magnetic resonance data to be acquired in said magnetic resonance data acquisition sequence at said same position of the patient's diaphragm in multiple respiratory cycles and only within said shimming window; and
   said controller being configured to operate said magnetic resonance data acquisition apparatus to adjust a homogeneity of said basic magnetic field in said shimming window using said DESS sequence or said FLASH sequence.

6. A non-transitory computer-readable storage medium encoded with programming instructions, said medium being loadable into a computer configured to operate a magnetic resonance system, said programming instructions causing said computer to:
   operate a magnetic resonance data acquisition apparatus with a magnetic resonance data acquisition sequence selected from the group consisting of a double echo steady state (DESS) sequence and a fast low angle shot (FLASH) sequence, to acquire magnetic resonance data in said magnetic resonance data acquisition sequence from a freely breathing patient located in a basic magnetic field generated in the magnetic resonance apparatus;
   monitor respiration of the examination subject in the magnetic resonance data acquisition apparatus using a two-dimensional prospective acquisition correction (2D PACE) signal to identify a shimming window that is identically correlated with the same physical, mechanical position of the patient's diaphragm in the respiratory cycle;
   operate an electrocardiogram (ECG) monitor to acquire an ECG from the patient in the magnetic resonance data acquisition apparatus;
   trigger acquisition of said magnetic resonance data with said magnetic resonance data acquisition sequence using said 2D PACE signal and said ECG to cause said magnetic resonance data to be acquired in said magnetic resonance data acquisition sequence at said same position of the patient's diaphragm in multiple respiratory cycles and only within said acquisition window; and
   operate said magnetic resonance data acquisition apparatus in said shimming window to adjust a homogeneity of said basic magnetic field using said DESS sequence or said FLASH sequence.

* * * * *